United States Patent [19]

Dyroff et al.

[11] 4,130,635

[45] Dec. 19, 1978

[54] CALCULUS INHIBITION

[75] Inventors: David R. Dyroff, Creve Couer, Mo.; Walton F. Suchanek, Jr., Belleville, Ill.

[73] Assignee: Monsanto Company, St. Louis, Mo.

[21] Appl. No.: 744,220

[22] Filed: Nov. 22, 1976

[51] Int. Cl.$^2$ .......................... A61K 7/16; A61K 7/24
[52] U.S. Cl. ..................................... 424/48; 424/49; 424/55
[58] Field of Search ................................. 424/48–58, 424/317

[56] References Cited

U.S. PATENT DOCUMENTS

| | | | |
|---|---|---|---|
| 3,542,917 | 11/1970 | Schwartz | 424/49 |
| 3,671,626 | 6/1972 | Felger | 424/49 |
| 3,887,616 | 6/1975 | Lannert | 260/535 P |
| 3,897,490 | 7/1975 | Lannert | 260/535 P |
| 3,920,837 | 11/1975 | Schmidt-Dunker et al. | 424/49 X |

FOREIGN PATENT DOCUMENTS

| | | |
|---|---|---|
| 2411383 | 9/1974 | Fed. Rep. of Germany. |
| 2108827 | 5/1972 | France. |
| 1376730 | 11/1974 | United Kingdom. |

OTHER PUBLICATIONS

Murata et al., Nippon Kagaku Kaishi 1974(9):1724–1730, "Effects of Physicochemical Properties of a Detergency Builder on the Detergency," USPTO Translation (3/7/78) 15 pp.

U.S.P.T.O. Translation–4/27/77 (10 pp.) of Loach Gor. Off. 2,411,383, Sep. 12, 1974.

U.S.P.T.O. Translation–3/31/77 (7 pp.) of Centre France 2,108,827, May 26, 1972.

*Primary Examiner*—Shep K. Rose
*Attorney, Agent, or Firm*—S. M. Tarter; E. P. Grattan; F. D. Shearin

[57] ABSTRACT

Oral compositions such as mouth washes, toothpastes, foods, chewing gums and the like containing certain carboxyalkoxy-hydroxyalkyl-propanedioic acids and/or salts thereof inhibit formation of dental calculus.

17 Claims, No Drawings

CALCULUS INHIBITION

BACKGROUND OF THE INVENTION

The field of this invention is "oral compositions" which term herein means products intended for introduction into the oral cavity in such a manner as to contact exposed dental surfaces therein. Examples of such products are human and lower animal foods, chewing gums and oral hygiene products including mouth washes, prophylaxis pastes, topical solutions and dentifrices such as toothpastes, tooth powders, dental creams and the like.

Dental calculus, or tartar as it is somtimes called, is a deposit which forms on the surfaces of teeth predominantly at or near the gingival margin. Supragingival calculus appears most heavy in areas near the orifices of the salivary ducts. Mature calculus contains an inorganic portion which is largely calcium phosphate arranged in a hydroxyapatite crystal lattice structure similar to that occurring in bone, enamel or dentine. An organic portion is typically also present consisting of desquamated epithelial cells, salivary sediment, food debris, various types of microorganisms, etc.

As calculus develops, it becomes visibly white or yellowish unless stained or discolored by some extraneous substance. In addition to being undesirable from an esthetic standpoint, mature calculus deposits are sources of irritation of the gingiva and thereby a contributing factor to gingivitis and other diseases of the supporting structures of the teeth, the irritation decreasing the resistance of tissues to endogenous and exogenous organisms.

Periodic mechanical removal of this material by a denstist or dental technician is routine dental office procedure. There have also been proposed a number of chemical agents for calculus removal. For example, alkali metal and ammonium diglycolates and diglycolates of organic bases such as urea, guanidine or ethanolamine are suggested for that use in U.K. Pat. No. 995,330 issued June 16, 1965 to R. A. Oetker. Similarly, in U.S. Pat. No. 3,429,963 issued Feb. 25, 1969 to L. Shedlovsky, it is taught that dental calculus can be removed by use of dental preparations containing a hydrolyzed copolymer of ethylene and maleic anhydride having an average molecular weight of at least about 1500.

In some instances, chemical agents have been said to be capable of retarding calculus formation. For example, in the aforementioned U.S. Pat. No. 3,429,963 it is disclosed that a reduction in calcuus formation was observed in rates when the drinking water given to the rats contained 1% of a hydrolyzed copolymer of ethylene and maleic anhydride. Another polymer, i.e., a polyester of a polycarboxylic acid having three or more carboxyl groups and a polyalkylene ether having at least two hydroxyl groups, is described as a calculus retarding agent in U.S. Pat. No. 3,542,917 issued Nov. 24, 1970 to A. M. Schwartz et al. In U.S. Pat. No. 3,920,837 issued Nov. 18, 1975 to M. Schmidt-Dunker et al, it is said that tartar formation can be substantially reduced by cyclohexanehexacarboxylic acid or its water-soluble salts. Various phosphorous compounds such as, e.g., ethane-1-hydroxy-1,1-diphosphonic acid (hereinafter EHDP), have also been proposed for such use in U.S. Pat. No. 3,488,419 issued Jan. 6, 1970 to H. W. McCune et al.

Some of the chemical agents heretofore proposed for calculus removal or retardation contain functional groups of uncertain effect on animals in terms of toxicity, side efects, etc. Certain other kinds of compounds containing only carbon, hydrogen, oxygen and possibly sodium, potassium or other pharmaceutically acceptable cations are believed essentially free from such uncertainty and therefore preferable for use in oral compositions. Also desirable for present purposes are compounds of relatively simple structure and low molecular weight, as well as compounds which can be prepared without resort to a polymerization process. Accordingly, oral compositions containing compounds which meet those criteria and which substantially inhibit dental calculus formation are highly desirable, and it is an object of this invention to provide such compositions. Other objects will be apparent from the following disclosure in which all percentages are by weight except where otherwise noted.

SUMMARY OF THE INVENTION

This invention is an oral composition effective in inhibiting formation of dental calculus, said composition comprising (1) a propanedioic acid compound selected from the group consisting of acids having the structural formula:

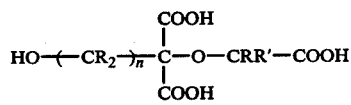

wherein R is hydrogen or lower alkyl, R' is lower alkyl and n is 1 or 2, and pharmaceutically acceptable salts of said acids and (2) a carrier suitable for use in the oral cavity, said compound being present in said composition amount and concentration sufficient to substantially inhibit formation of dental calculus.

DESCRIPTION OF PREFERRED EMBODIMENTS

In the foregoing formula each R can be the same as or different from any other R in that formula. In particular, when n is 2, the R's directly attached to one of the carbon atoms linking the hydroxy and propanedioic acid groups in that formula can be the same as or different from the R's attached to the other carbon atom linking those groups. Also as used herein, "lower alkyl" means $C_1$-$C_4$ alkyl groups which can be branched (e.g. isopropyl, isobutyl or tert-butyl) or cyclic (cyclopropyl or cyclobutyl) but which are preferably straight-chain (methyl, ethyl, n-propyl or n-butyl).

In many embodiments of the invention it is preferred that, when n the foregoing formula is 1, at least one R in the —$CR_2$— radical is hydrogen and the other R in that radical is hydrogen, methyl or ethyl. In some of those embodiments it is even more preferred that, when n is 1, each R in the —$CR_2$— radical is hydrogen. In some embodiments it is preferred that each alkyl group in the —CRR'— radical is normal alkyl, and in some cases it is very desirable that the number of carbon atoms in the —CRR'— radical is not greater than 5. In some embodiments it is further preferred that R' is methyl or ethyl and the R in the —CRR'— radical is hydrogen. In many embodiments it is especially preferred that R is hydrogen, particularly when n is 1, and it is also generally preferable that n is 1. Another special preference is that R' is methyl. Each of these embodiments is preferable on the basis of relatively low molecular weight. On the other hand, some compounds similar to those expressly included in that formula but wherein one or more of the R's and/or the R' in that formula contains more than four carbon atoms may similarly inhibit calculus formation when used in suitable oral compositions and in such cases should be regarded as equivalents of the aforementioned propanedioic acid compounds for purposes of this invention.

The propanedioic acid compounds represented by the foregoing formula are herein designated 2-(carboxyalkoxy)-2-(hydroxyalkyl)-propanedioic acids, and the compound in which R is hydrogen, R' is methyl and n is 1 is designated 2-(1-carboxyethoxy)-2-(hydroxymethyl)-propanedioic acid (hereinafter for convenience called CEHMPDA). The trisodium salt of that acid can be prepared by procedure set forth in U.S. Pat. No. 3,897,490 issued July 29, 1975 to Kent P. Lannert, the disclosure of which is incorporated herein by reference. Similar salts of other acids represented by that formula when n is 1 and in which R' is $C_2$-$C_4$ alkyl and/or the R in the —CRR'— radical is lower alkyl can be prepared by procedure analogous to that in U.S. Pat. No. 3,897,490 but in which an appropriate conjugate base of a lower alkyl ester of a more highly alkyl-substituted α-hydroxy acid (e.g. α-hydroxy-n-butyric, -isobutyric, -isovaleric or the like) is used instead of one of the α-hydroxy ester salt reactants suggested in that patent. Similar salts of other acids represented by that formula when n is 1 and at least one R directly attached to the hydroxylated carbon atom in that formula is lower alkyl can be prepared by procedure analogous to that in U.S. Pat. No. 3,897,490 but in which there is substituted for the formaldehyde reactant a different aldehyde (e.g. acetaldehyde when one such R is methyl and the other such R is hydrogen) or the appropriate ketone (e.g. acetone when both such R's are methyl) and in which the hydroxy radical is shielded during the ester hydrolysis step by a suitable protecting group (e.g. dihydropyran) that can be subsequently removed, e.g. by mild acid hydrolysis.

The trisodium salts of acids represented by the foregoing formula when n is 2, R' is methyl or ethyl and the R in the —CRR'— radical is hydrogen can be prepared by procedure set forth in U.S. Pat. No. 3,887,616 issued June 3, 1975 to Kent P. Lannert, which disclosure is also incorporated herein by reference. Similar salts of other acids represented by that formula when n is 2 and in which R' is $C_3$-$C_4$ alkyl and/or the R in the —CRR'— radical is lower alkyl can be prepared by procedure analogous to that in U.S. Pat. No. 3,887,616 but in which an appropriate conjugate base of a lower alkyl ester of a more highly alkyl-substituted α-hydroxy acid (e.g. α-hydroxy-n-valeric, -isobutyric, -α-methyl-n-valeric or the like) is used instead of one of the α-hydroxy ester salt reactants suggested in that patent or, in the alternate preparation described in that patent, an appropriate lower alkyl ester of a more highly alkyl-substituted haloacid (e.g. α-bromo-n-valeric, -isobutyric, -α-methyl-n-valeric or the like) is used instead of one of the haloester reactants suggested in that patent.

Any of the aforementioned propanedioic acid salts can be converted to the corresponding acid (e.g. CEHMPDA) by treatment with a strong acid, e.g. HCl, $H_2SO_4$ or a strongly acidic ion exchange resin. Other metal salts of the resulting acids can be prepared by neutralization with the appropriate metal hydroxide, e.g. an alkali metal hydroxide such as potassium hydroxide. The corresponding ammonium, mono- or di($C_1$-$C_3$ alkyl)-ammonium or mono- or di($C_1$—$C_3$ alkanol)ammonium salts can be prepared by treating such acids with ammonia, an appropriate alkylamine or alkanolamine or hydroxide thereof in accordance with procedures well known in the art.

In the oral compositions of this invention, the proportions in which the aforementioned propanedioic acid compounds are present as acids and/or partially-substituted or fully-substituted salts thereof are dependent on the pH of the composition. That pH normally between about 4 and about 11, although in some instances it may be higher or lower than that range. Below about pH 4 there is a greater danger of damage to dental enamel despite the relative safety of the aforementioned acid or its salts. Above about pH 11, greater difficulty is encountered in formulating products having satisfactory flavor and mildness. A preferred pH range is from about 6 to about 10. In many embodiments, the pharmaceutically acceptable salts employed are preferably water-soluble salts such as, e.g., sodium, potassium or ammonium salts, to facilitate their dissolution in saliva.

Some embodiments of this invention are oral hygiene products such as dentifrices, mouth washes, prophylaxis pastes and topical solutions. A dentifrice, especially toothpaste, containing a calculus-inhibiting amount of an acid represented by the foregoing formula and/or a pharmaceutically acceptable salt thereof is a preferred embodiment of this invention. A mouth wash containing such an acid and/or salt is another preferred embodiment. Except for inclusion of a propanedioic acid compound as described hereinbefore, many formulations of such products are well known in the art. For example, typical formulations of toothpastes and mouth washes compatible with calculus-inhibiting compounds of the kind employed in accordance with this invention are described in U.S. Pat. Nos. 3,639,569 issued Feb. 1, 1972 to R. F. Medcalf, Jr., 3,544,678 issued Dec. 1, 1970 to W. J. Griebstein, 3,678,154 issued July 18, 1972 to J. S. Widder et al and 3,959,458 issued May 25, 1976 to F. O. Agricola et al, the disclosures of which are incorporated herein by reference.

Under conditions of normal use, the oral compositions of this invention are pharmaceutically acceptable, i.e., capable of introduction into the oral cavity without significant adverse effect in tooth structure or other injury to health. Subject to the limits of such pharmaceutical acceptability, the calculus-inhibiting amounts and concentrations of the aforementioned propanedioic acid compounds can be varied widely in the oral compositions of this invention. Such amounts and concentrations are also readily definable for each kind of oral composition by formulators skilled in the art. Generally, concentrations from 0.01% to about 10% are preferred. Oral compositions which in ordinary usage may be accidentally or intentionally ingested can contain relatively low but still highly effective concentrations. Of course, any such ingested composition should be physiologically (i.e., digestively) acceptable. Thus, a mouth wash in accordance with this invention typically contains between about 0.1 and about 3% of the aforementioned calculus-inhibiting compound. Dentifrice compositions, topical solutions and prophylaxis pastes, the last normally administered professionally, may desirably contain up to about 10% or even more thereof but usually contain between about 0.1 and about 5% and even more typically between about 1 and about 2% thereof.

While it is not intended that this invention be limited to any particular theory of operation, it has been observed that the aforementioned propanedioic acid compounds appear to inhibit calculus formation by interfering with the conversion of dissolved calcium phosphate in saliva to crystalline deposits in the nature of calcium hydroxyapatite. Hence the compositions of this invention preferably do not contain soluble polyvalent cations in an amount likely to deplete the crystal growth inhibiting capacity of those compounds to the extent that their calculus formation inhibiting activity would be essentially neutralized.

The following specific examples are illustrative only and do not imply any limitations on the scope of the invention.

EXAMPLES I-V

A. Evaluations of Calculus Inhibition

Evaluations of the effectiveness of compounds employed in accordance with this invention to inhibit calculus formation were carried out fundamentally as described in "A Method and Apparatus for Studying In Vitro Calculus" by S. Yankelowitz et al of the Colgate-Palmolive Co., Journal of Dental Research 44 (No. 4),648-53 (1965). In accordance with that method, now well known in the art, simulated oral calculus deposits are caused to be formed on glass slides by mechanically rotating the slides edgewise and vertically at 0.5 rpm in such a way that each slide passes alternately through a small sample of whole human saliva containing 0.1% of added monocalcium phosphate and then through a forced draft of air which at least partially dries each slide before it passes again through that saliva sample. As stated in the journal article just mentioned, the resulting calculus deposits have been found similar to oral calculus deposits in both composition and X-ray diffraction pattern.

In the present evaluations, 150 mls of stimulated saliva were collected over a three-day period (50 ml/day) from a donor whose saliva had been previously found to have a substantial tendency toward calculus formation. The collected saliva was also of a type in which, under the conditions of this test, calculus formation is inhibited by EHDP substantially more than by water substituted for the EHDP in a comparative test run. Each 50 ml portion of the saliva was kept frozen until ready for use. At that time the combined 150 ml sample was neutralized to pH 7± .05 after addition of the 0.1% of monocalcium phosphate, thoroughly stirred and then divided into 25 ml aliquots. To one aliquot was added 1 ml of a 0.1 M solution of the trisodium salt of CEHMPDA, and to a second aliquot was added 1 ml of a 0.1 M solution of the prior art anti-calculus compound EHDP, each of those solutions having been previously neutraized with NaOH or $H_2SO_4$. To a third aliquot was added 1 ml of distilled water.

For comparative test purposes, the three aliquots were then placed in identical side-by-side trough-like containers in an oven equipped with apparatus adapted to rotate a separate set of three 22 × 40 mm glass slides (spaced about 120° apart in relation to the rotating shaft on which they were mounted) through each of the saliva containers and to maintain a steady horizontal flow of air against the sides and perpendicular to the axis of their rotation. All slides used were essentially identical and mounted in the shaft such that the same portion (24 mm) of the length of each slide passed through the appropriate saliva sample.

In the oven just described, the calculus formation test was continued for 20 consecutive hours with the interior of the oven maintained at 37±1° C and a relative humidity between 76 and 78%. The saliva samples were then removed from the oven, after which rotation of the slides in the flow of air was continued for an additional hour before removal of the slides from the oven. The weight of each slide and any deposit remaining thereon was then compared with the weight of the slide prior to its use in this test, and visual appraisals of the deposits were made using photographs taken of each slide under identical conditions to further eliminate variables from those appraisals. Results were recorded separately for each of the three slides in each set and then averaged. Thereafter, the entire procedure was repeated using saliva from the same donor and then repeated again using saliva from a different donor, after which the averaged results of the two runs using saliva from the same donor were averaged with the results of the run using saliva from a different donor to provide the results reported hereinafter.

In these tests it was found that the weights of simulated calculus on the slides that had been exposed to the salivas containing the trisodium salt of CEHMPDA averaged 0.58mg. those on the slides used in the comparative runs with EHDP averaged 0.44 mg, and those on the slides used in the comparative runs with water averaged 0.83 mg. Thus in the runs using the trisodium salt of CEHMPDA, formation of the simulated calculus averaged 30% less than in the comparative runs using water, while in the comparative runs using EHDP it averaged 47% less than in the comparative runs using water. In the visual appraisal, the amounts of opaque material deposited on the slides that had been exposed to the salivas containing the trisodium salt of CEHMPDA were judged to be no higher than 33 and, on average, below 25 on an essentially linear scale in which 100 represents the amount of opaque material in the slides used in the comparative runs with water and 0 represents the amount of such material on the slides used in the comparative runs with EHDP. Also in the visual appraisal, the amounts of opaque material deposited on the slides exposed to the salivas containing the CEHMPDA salt were judged to be, on average, substantially less than half as great as those on the slides used in the comparative runs with water.

B. Preparation of Oral Compositions

The compound tested in Part A of these examples, the corresponding acid and other pharmaceutically acceptable salts of that acid are useful for inhibition of dental calculus formation when incorporated in compatible carriers or vehicles of any of the usual types. The following are examples of mouth wash compositions comprising at least one of such compounds.

| Component | Examples | | | |
|---|---|---|---|---|
| | I | II | III | IV |
| | Parts by weight | | | |
| Glycerine | 10.0 | 10.0 | 10.0 | 10.0 |
| Ethyl alcohol | 16.5 | 16.5 | 16.5 | 16.5 |
| Water | 67.172 | 67.172 | 67.172 | 70.192 |
| Tween 80[1] | .12 | .12 | .12 | .12 |
| Saccharin | .045 | .045 | .045 | .02 |
| Sodium cyclamate | 0.75 | 0.75 | 0.75 | .04 |
| Flavor | .088 | .088 | .088 | .088 |
| Salt of CEHMPDA | [2]3.0 | [3]4.0 | [4]2.0 | [5]1.8 |

-continued

| Component | Examples | | | |
|---|---|---|---|---|
| | I | II | III | IV |
| | Parts by weight | | | |
| pH[6] | 7.0 | 7.0 | 8.5 | 10.0 |

[1]Polyoxyethylene (20 moles of ethylene oxide) sorbitan monoleate - a nonionic emulsifier supplied by Atlas Powder Co.
[2]Triammonium salt.
[3]Tri(triethanolammonium) salt.
[4]Trisodium salt.
[5]Tripotassium salt.
[6]Adjusted to value indicated with NaOH or $H_2SO_4$.

The following is an example of a toothpaste composition comprising at least one of such compounds.

| Component | Example V Parts by weight |
|---|---|
| Water | 31.58 |
| Sorbitol | 6.25 |
| Saccharin | 0.12 |
| Calcium pyrophosphate[1] | 39.00 |
| Glycerine | 18.00 |
| Sodium alkyl (coconut) sulfate | 0.40 |
| Sodium coconut monoglyceride sulfonate | 0.75 |
| Sodium carboxymethyl cellulose | 1.15 |
| Magnesium aluminum silicates | 0.40 |
| Flavoring | 0.85 |
| CEHMPDA | 1.00 |
| pH[2] | 5.90 |

[1]Prepared in accordance with U.S. Patent 3,112,247 granted November 26, 1963.
[2]Adjusted to indicated pH with sodium hydroxide.

Other examples of tootpaste compositions comprising at least one of the aforementioned propanedioic acid compounds are substantially identical to the toothpaste composition above except for substitution the corresponding potassium or ammonium salt of CEHMPDA or the similar sodium, potassium or ammonium salt of 2-(1-carboxyethoxy)-2-(2-hydroxyethyl)-propanedioic acid, 2-(1-carboxypropoxy)-2-(hydroxymethyl)-propanedioic acid or 2-(1-carboxy, 1-methylethoxy)-2-(hydroxymethyl)-propanedioic acid.

Additional examples of oral compositions comprising at least one of such compounds include other mouth washes and toothpastes, tooth powders, dental creams and prophylaxis pastes for use by a dentist or dental technician in polishing of teeth after removal of calculus deposits. Examples of such compositions, except for inclusion of a calculus-inhibiting compound of the kind used in accordance with the present invention, are described in the aforementioned U.S. Pat. Nos. 3,544,678, 3,639,569, 3,678,154 and 3,959,458. Other examples of oral compositions comprising at least one of the compounds used in accordance with this invention include human foods such as soft drinks, candies, pastries, etc., foods for pets or livestock, chewing gums, etc. The ingredients of such compositions (other than the aforementioned propanedioic acis and salts thereof) as well as various mixtures of such ingredients are illustrative of carriers suitable for use in the oral cavity in accordance with the present invention.

The embodiments of this invention in which an exclusive property or privilege is claimed are defined as follows:

1. An oral composition effective in inhibiting formation of dental calculus, said composition comprising (1) a propanedioic acid compound selected from the group consisting of acids having the structural formula:

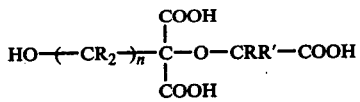

wherein R is hydrogen or lower alkyl, R' is lower alkyl, n is 1 or 2 and each R can be the same as or different from any other R in said formula, and pharmaceutically acceptable salts of said acids and (2) a carrier suitable for use in the oral cavity, said compound being present in said composition in amount and concentration sufficient to substantially inhibit formation of dental calculus.

2. A composition according to claim 1 wherein said carrier comprises a dental abrasive, flavoring agent, chewing gum base material, or human or animal food.

3. A composition according to claim 2 wherein, when n is 1, one R in the —$CR_2$— radical is hydrogen and the other R in said radical is hydrogen, methyl or ethyl.

4. A composition according to claim 2 wherein, when n is 1, each R in the —$CR_2$— radical is hydrogen.

5. A composition according to claim 4 wherein each alkyl group in the —CRR'— radical is normal alkyl and the number of carbon atoms in the —CRR'— radical is not greater than 5.

6. An oral hygiene composition according to claim 5.

7. A chewing gum composition according to claim 5.

8. A composition accordng to claim 5 wherein R is hydrogen.

9. A composition according to claim 8, said compound being selected from the group consisting of alkali metal and ammonium salts of said acids.

10. An oral hygiene composition according to claim 9.

11. A food composition according to claim 9 to be ingested by humans or lower animals.

12. A composition according to claim 8 wherein n is 1.

13. A composition according to claim 12 wherein R' is methyl.

14. An oral hygiene composition according to claim 13.

15. A composition according to claim 14, said compound being selected from the group consisting of alkali metal and ammonium salts of said acid.

16. A mouth wash composition according to claim 13 having a pH between about 4 and about 11 wherein said carrier comprises a flavoring agent.

17. A toothpaste composition according to claim 13 having a pH between about 4 and about 11 wherein said carrier comprises a dental abrasive or a flavoring agent.

* * * * *

UNITED STATES PATENT AND TRADEMARK OFFICE
CERTIFICATE OF CORRECTION

PATENT NO. : 4,130,635
DATED : December 19, 1978
INVENTOR(S) : David R. Dyroff and Walton F. Suchanek, Jr.

It is certified that error appears in the above–identified patent and that said Letters Patent are hereby corrected as shown below:

"[75] Inventors: David R. Dyroff, Creve Coeur, Mo.; Walton F. Suchanek, Jr., Belleville, Ill." should be --- Inventors: David R. Dyroff, Creve Coeur, Mo.; Walton F. Suchanek, Jr., Belleville, Ill.; and Thomas G. Schiff, Clayton, Mo. ---.

Signed and Sealed this

Twentieth Day of March 1979

[SEAL]

Attest:

RUTH C. MASON
Attesting Officer

DONALD W. BANNER
Commissioner of Patents and Trademarks